United States Patent
Kinoshita et al.

(10) Patent No.: US 6,926,958 B2
(45) Date of Patent: Aug. 9, 2005

(54) BASE FILM FOR MEDICAL ADHESIVE TAPE, AND MEDICAL ADHESIVE TAPE, ADHESIVE PLASTER AND FIRST-AID ADHESIVE TAPE PRODUCED USING THE FILM

(75) Inventors: Takashi Kinoshita, Osaka (JP); Atsushi Hamada, Osaka (JP); Tetsuo Watanabe, Osaka (JP); Fumiya Shirai, Osaka (JP); Kenji Furumori, Osaka (JP)

(73) Assignee: Nitto Denko Corporation, Osaka (JP)

( * ) Notice: Subject to any disclaimer, the term of this patent is extended or adjusted under 35 U.S.C. 154(b) by 104 days.

(21) Appl. No.: 09/829,985

(22) Filed: Apr. 11, 2001

(65) Prior Publication Data

US 2001/0051782 A1 Dec. 13, 2001

(30) Foreign Application Priority Data

Apr. 20, 2000 (JP) .................................... P. 2000-119987

(51) Int. Cl.$^7$ ........................... B32B 15/04; B32B 7/12; B32B 27/08; B32B 27/32
(52) U.S. Cl. ................... 428/343; 428/354; 428/355 R; 428/515; 428/516; 428/517; 428/519; 428/521
(58) Field of Search ................................ 428/343, 354, 428/355 R, 515, 516, 517, 519, 521

(56) References Cited

U.S. PATENT DOCUMENTS

| 3,607,616 A | 9/1971 | Barbehenn et al. |
| 5,134,012 A | 7/1992 | Arakawa et al. |
| 5,264,281 A | 11/1993 | Arakawa et al. |
| 5,432,009 A | 7/1995 | Tabata et al. |
| 5,616,420 A | * 4/1997 | Yamaoka et al. ........... 428/515 |
| 5,795,834 A | 8/1998 | Deeb et al. |

FOREIGN PATENT DOCUMENTS

EP 0 533 493 A1 3/1993

* cited by examiner

*Primary Examiner*—Terrel Morris
*Assistant Examiner*—Victor Chang
(74) *Attorney, Agent, or Firm*—Sughrue Mion, PLLC

(57) ABSTRACT

A base film for medical adhesive tape is described, which is obtained by laminating, over one side or both sides of layer A composed of amorphous polyolefin, layer B composed of a polypropylene-based resin. A medical adhesive tape equipped with a pressure-sensitive adhesive layer on at least one side of the base film for medical adhesive tape; an adhesive plaster obtained by rolling the medical adhesive tape having the base film equipped with the pressure-sensitive adhesive layer; and a first-aid adhesive tape comprising the medical adhesive tape having the base film equipped with the pressure-sensitive adhesive layer and a liquid-absorbing pad disposed in a central region of the pressure-sensitive adhesive layer are also described.

10 Claims, No Drawings

BASE FILM FOR MEDICAL ADHESIVE TAPE, AND MEDICAL ADHESIVE TAPE, ADHESIVE PLASTER AND FIRST-AID ADHESIVE TAPE PRODUCED USING THE FILM

FIELD OF THE INVENTION

The present invention relates to a base film for a medical adhesive tape, and a medical adhesive tape, adhesive plaster and first-aid adhesive tape each produced using the base film. More specifically, the invention pertains to a medical adhesive tape suited for use, for example, in a rolled adhesive plaster, a first-aid adhesive tape, a cataplasm, a dressing or a wound protector, particularly to a medical adhesive tape suitably used for the aged, infants or sickly persons sensitive to stimulation to the skin.

BACKGROUND OF THE INVENTION

A number of films composed mainly of plasticized polyvinyl chloride and formed by calendering or casting method have conventionally been employed as a base film used for medical adhesive tapes such as first-aid adhesive tape and rolled adhesive plaster.

The films composed mainly of plasticized polyvinyl chloride are characterized in that when they are left under tension, a high stress at the initial stage relaxes drastically with the passage of time. When a medical adhesive tape composed of a film having such a characteristic is applied to the skin, tensile stress is relaxed gradually after application, resulting in the relief of the burden to the skin.

In recent years, however, it has been requested to take countermeasures against the use of plasticized polyvinyl chloride from the viewpoint of environmental pollution caused by a phthalic acid liquid plasticizer used for it or chlorine contained in it. In addition, it has been pointed out that a large amount of a liquid plasticizer added to plasticized polyvinyl chloride to impart flexibility thereto transfers into a pressure-sensitive adhesive, thereby lowering the cohesion of a pressure-sensitive adhesive layer and causes problems such as so-called adhesive residue and deterioration of pressure-sensitive adhesive force.

A thermoplastic resin having both flexibility and stretch property is under brisk development as a substitute for polyvinyl chloride not only in the medical field but also in another field.

Examples of such a substitute include ethylene-methacrylate-based resin, poly-α-olefin-based resin, ethylene-vinyl acetate-based resin, polyurethane-based resin, and low-density polyethylene-based or linear low-density polyethylene-based resin. Moreover, a medical adhesive tape having a pressure-sensitive adhesive laminated over a substrate base material, which has been imparted with flexibility and strength by incorporating, as a modifier, a different kind of a thermoplastic elastomer in such a resin, is now studied and developed.

Under the present situation, however, a medical adhesive tape produced using a single film or blend film composed of such a resin has not yet fully reached the level of a medical adhesive tape composed of a plasticized polyvinyl chloride (plasticized polyvinyl chloride) film well-balanced in heat resistance, tensile strength, flexibility and stress relaxation.

SUMMARY OF THE INVENTION

In consideration of the above-described problems of the prior art, the invention has been completed. An object of the present invention is to provide a novel base film for a medical adhesive tape which is substitutable for a plasticized polyvinyl chloride film having properties well balanced in tensile strength, flexibility and stress relaxation.

The present inventors have carried out an extensive investigation. As a result, it has been found that a multilayer film produced using an amorphous polyolefin film as a substrate base material has properties close to those of a plasticized polyvinyl chloride film in tensile strength, flexibility and stress relaxation. It has also been found that in such a film, bleed-through of the low-molecular-weight substance contained in the film and serving to impart it with flexibility can be suppressed, leading to the completion of the invention.

The base film for a medical adhesive tape according to the invention is characterized by laminating layer B composed of a polypropylene-based resin over at least one side of layer A composed of amorphous polyolefin. In other words, the base film for a medical adhesive tape according to the invention has a structure formed of at least two layers, that is, a film (layer A) composed of amorphous polyolefin and another film (layer B) composed of a polypropylene-based resin. The present invention also embraces a base film formed by laminating layer B's over both sides of layer A.

DETAILED DESCRIPTION OF THE INVENTION

The base layer (layer A) of the base film for a medical adhesive tape according to the invention is composed mainly of amorphous polyolefin and it is prepared by incorporating an inorganic filler and a high-molecular plasticizer in amorphous polyolefin as needed.

Examples of the amorphous polyolefin include that available by the process as disclosed in JP-A-4-224809 (the term "JP-A" as used herein means an "unexamined published Japanese patent application") or that described in JP-B-6-89071 (the term "JP-B" as used herein means an "examined published Japanese patent application"). Specific examples include that obtained by atactic polymerization of propylene alone in the presence of a catalyst and that having a relatively low molecular weight and obtained by copolymerizing propylene and an α-olefin, which is other than propylene and has 2 to 10 carbon atoms, to arrange the monomers at random. In the latter case, amorphous polyolefin having a propylene content of 50 wt. % or greater based on the whole weight of the monomers and having a $C_{2-10}$ α-olefin content not greater than 50 wt. % based on the whole weight of the monomers is preferred.

Examples of the α-olefin include chain α-olefins such as ethylene, butene-1, pentene-1, hexene-1, octene-1, nonene-1, decene-1, 4-methylpentene-1, 4-methylhexene-1 and 4,4-dimethylpentene-1 and cyclic α-olefins such as cyclopentene and cyclohexene. These α-olefins may be used either singly or in combination of two or more. Among them, amorphous propylene polymers and amorphous copolymers of ethylene and/or butene-1 and propylene, that is, a copolymer of ethylene and propylene, a copolymer of butene-1 and propylene and a random copolymer of ethylene, butene-1 and propylene are particularly preferred. The term "amorphous polyolefin" as used herein means not only amorphous polyolefin but also polyolefin having crystallinity low enough not to impair the advantages of the invention.

As amorphous polyolefin, those having a number average molecular weight of 1,000 to 28,000, preferably 1,500 to 25,000, more preferably 2,000 to 20,000 and having a relatively low melt viscosity at 190° C. of 100 to 100,000 mPa·S are preferred.

Use of such an amorphous or low-crystallinity polyolefin, a crystalline portion of which has been reduced largely compared with that of the conventionally employed polypropylene resin, makes it possible to heighten stress relaxation and flexibility of a base film for a medical adhesive tape.

In the invention, a crystalline polypropylene-based resin may be mixed as needed in order to adjust physical properties such as modulus of elasticity or elongation. It is preferred to adjust the mixing ratio of amorphous (low-crystallinity) polyolefin to 5 to 95 wt. %, preferably 10 to 90 wt. %, more preferably 20 to 80 wt. %, based on the whole weight of the resins. At an amount of amorphous (low crystallinity) polyolefin less than 5 wt. % based on the whole weight of the resins, the base film for a medical adhesive tape available therefrom tends to have deteriorated flexibility and is not suited for the using purpose of the invention.

In order to impart a medical adhesive tape base film with the properties of a plasticized film, it is particularly preferred to use, as crystalline polypropylene to be mixed, a propylene-based random copolymer having a density of 0.890 g/cm³ or greater, preferably 0.895 g/cm³.

As amorphous (low crystallinity) polyolefin or crystalline polypropylene, modified polyolefin is also usable in the invention. Examples of the modified polyolefin include those available by modifying the above-exemplified amorphous (low crystallinity) polyolefin or crystalline polyolefin with an unsaturated carboxylic acid such as acrylic acid, methacrylic acid, maleic acid, fumaric acid or itaconic acid, or an ester, acid anhydride, or metal salt thereof, or a derivative thereof.

As described above, 10 to 75 wt. %, based on the whole weight of layer A, of an inorganic filler is preferably incorporated in layer A. Although there is no particular limitation imposed on the inorganic filler insofar as it is conventionally added to a film. Examples include silicic acid compounds such as zeolite, bentonite, mica, talc, calcium silicate, silica, kaolin, glass fibers and clay.

Among them, zeolite and talc are suited for use in the invention because they can improve stress relaxation without increasing the rigidity of the film as layer A compared with another silicic acid compound.

In the invention, zeolite can be used freely whether it is natural or synthetic. Examples of natural zeolite include mordenite, erionite, clinoptilolite and chabazite, while those of synthetic zeolite include Zeolite A, Zeolite X, Zeolite Y, Zeolite L and omega zeolite. At least one or a mixture of at least two of those selected from the above-exemplified ones can be used.

Although no particular limitation is imposed on the particle size of the inorganic filler, that having an average particle size of 0.01 to 150 μm, preferably 0.5 to 100 μm, more preferably 0.5 to 35 μm is desired. Use of an inorganic filler having an average particle size exceeding 150 μm is not preferred, because it causes dispersion failure and the base film for medical adhesive tape thus obtained is troubled with an increase in a so-called fish eye phenomenon.

Layer A further contains a thermoplastic elastomer. The addition of a thermoplastic elastomer as one component of layer A makes it possible to heighten the compatibility between the inorganic filler and polypropylene-based resin, thereby preventing a deterioration in impact resistance, stretch properties, flexibility and transparency of the medical adhesive tape base film thus obtained.

As such a thermoplastic elastomer, a low crystallinity elastomer not having a clear yield point and an amorphous elastomer having neither a clear melting point nor clear yield point and at the same time, each having rubber elasticity at normal temperatures can be used. Examples include styrene-based elastomers, olefin-based elastomers, polyester-based elastomers and polyamide-based elastomers.

Examples of styrene-based elastomers include styrene-butadiene copolymer and hydrogenated product thereof, styrene-butadiene-styrene copolymer (SBS), hydrogenated ethylene-butadiene-styrene copolymer (SEBS), isoprene-styrene copolymer and hydrogenated product thereof, hydrogenated styrene-isoprene copolymer (SEPS), hydrogenated styrene-vinyl isoprene copolymer (V-SEPS), styrene-isoprene-styrene copolymer (SIS) hydrogenated styrene-isoprene-styrene copolymer (SEPS) and hydrogenated styrene-butadiene-olefin crystal block copolymer (SEBC).

Examples of polyolefin-based elastomers include amorphous or low crystallinity polyolefin/α-olefin copolymers such as ethylene-propylene copolymer, ethylene-butene-1 copolymer, mixture of a polyolefin resin and an olefin-based rubber, a mixture of a polyolefin resin and a partially crosslinked olefin-based rubber and a mixture of a polyolefin resin and a completely crosslinked olefin-based resin.

Examples of polyester-based elastomers include polyester-polyether copolymer and polyester-polyester copolymer, while examples of polyamide-based elastomers include polyamide-polyester copolymer and polyamide-polyether copolymer.

Such a thermoplastic elastomer is added in an amount of 3 to 50 wt. %, more preferably 5 to 40 wt. % based on the whole weight of the resin composition of layer A. It is added in an amount of 5 to 30 wt. % based on the whole weight of layer A containing additives including the inorganic filler.

In the invention, a film (layer B) composed of a polypropylene-based resin is laminated over at least one side of such layer A. As this polypropylene-based resin, homopolypropylene is usable, but use of a copolymer composed mainly of propylene is desired. When homopolypropylene is employed, the resulting medical adhesive tape base film tends to have an increased modulus of elasticity.

As the copolymer, any one copolymerizable with propylene can be employed, but ethylene-containing random polypropylene is particularly preferred for obtaining appropriate flexibility.

In the invention, layer B is preferred to contain the above-described thermoplastic elastomer. The thermoplastic elastomer is added in an amount of 3 to 95 wt. %, more preferably 5 to 80 wt. % based on the whole weight of the resin composition of layer B. Based on the whole weight of layer B containing another additive, the thermoplastic elastomer is added in an amount of 10 to 50 wt. %.

The base film for a medical adhesive tape is provided as a two-layer film obtained by laminating layer B containing a thermoplastic elastomer over one side of layer A or a three-layer film obtained by laminating layer B over both sides of layer A. Particularly preferred is a three-layer structure obtained by laminating layer B containing a thermoplastic elastomer over one of the exposed surfaces of layer A and then laminating layer B containing or not containing a thermoplastic elastomer over the other one of the exposed surfaces of layer A. The base film for a medical adhesive tape having such a structure is capable of exhibiting properties close to those of a plasticized polyvinyl chloride film in heat resistance, tensile strength, flexibility and stress relaxation. The above-described base film and a plasticized polyvinyl chloride film are also similar in properties upon application, when a pressure-sensitive adhesive layer is laminated thereover. It is needless to say that laminating of layer B containing a thermoplastic elastomer or even layer B not containing a thermoplastic elastomer over only one of the two sides of layer A contributes to improvements in tensile strength, flexibility and stress relaxation to some extent.

Additives ordinarily employed for a medical adhesive tape base film such as heat stabilizer, antioxidant, photostabilizer, antistatic agent, lubricant, nucleating agent, flame retardant and/or pigment may of course be added to layer A and/or layer B.

In the invention, layer B (film) which is composed of a polypropylene-based resin and has a thermoplastic elastomer incorporated or not incorporated therein is laminated over layer A (film) which is composed of amorphous polyolefin and has an inorganic filler and thermoplastic elastomer optionally incorporated therein. Upon laminating, components of each layer are mixed and then, usually provided in the form of pellets or a mass, followed by processing into a laminate film.

No particular limitation is imposed on the mixing method. The components thus supplied are heated, melted and kneaded in an ordinarily-employed and well-known mixer, for example, kneader, roll or Banbury mixer, or by a single-screw or twin-screw extruder, and then the resulting mass is pelletized.

The laminate film made of layers A and B is formed from the pellets thus obtained. No particular limitation is imposed on the forming method. By the conventionally known T-die method, inflation method, calendering method or rolling method, the pellets are formed into a laminate film having a desired thickness. It is needless to say that components of each layer are kneaded and dry blended into a film continuously without a pelletizing step.

The laminate film can also be obtained by the conventionally-employed well-known method, that is, by laminating layer B on one side or both sides of layer A or coextrusion of two or three layers.

Layer A is adjusted to have a thickness of 10 to 100 $\mu$m, preferably 20 to 80 $\mu$m, while layer B, whether it contains a thermoplastic elastomer or not, is adjusted to have a thickness of 2 to 20 $\mu$m, preferably 3 to 15 $\mu$m. When the thickness of layer A is less than 10 $\mu$m, stress relaxation, which is one of the advantages available by the invention, cannot always be exhibited fully. When the thickness of layer A exceeds 100 $\mu$m, on the other hand, the resulting base film for a medical adhesive tape becomes too hard and lacks in flexibility, leading to a possibility of inducing a feeling of physical disorder upon application.

When the thickness of layer B is less than 2 $\mu$m, surface bleeding of a low-molecular weight substance of the resin used for layer A presumably occurs. When the thickness of layer B exceeds 20 $\mu$m, on the other hand, the modulus of elasticity becomes too high, leading to a possibility of inducing a feeling of physical disorder upon application.

Over one side or both sides of the thus formed base film for a medical adhesive tape, a pressure-adhesive layer is formed. The pressure-sensitive adhesive layer may be formed either on the surface of layer A or layer B, but the latter is preferred in consideration of the bleed-through of the low-molecular-weight substance contained in layer A or anchoring property. More preferred is the formation of the pressure-sensitive adhesive layer over the surface of the thermoplastic-elastomer-containing layer B for decreasing feeling of physical disorder upon application or preventing breakage of anchorage and by it, characteristics of the resulting base film can be brought more closer to those attained by a polyvinyl chloride film.

The pressure-sensitive adhesive layer can be formed over the medical adhesive tape base film either directly or indirectly. The latter is preferred. For example, the surface on which the pressure-sensitive adhesive layer is to be formed is embossed in order to improve the anchoring power with the base film, or is subjected to corona discharge treatment or pre-treatment with a primer in accordance with the conventionally known method.

No particular limitation is imposed on the pressure-sensitive adhesive layer. Any one conventionally used as a medical pressure-sensitive adhesive can be used. Examples include acrylic, rubber-based and silicone-based pressure-sensitive adhesives.

Examples of the acrylic pressure-sensitive adhesive include homopolymers of an alkyl (meth)acrylate preferably having 1 to 18 carbon atoms, more preferably 4 to 12 carbon atoms and copolymers available by copolymerizing the alkyl methacrylate, as a main monomer, with 1 to 50 wt. %, preferably 3 to 40 wt. %, based on the whole weight of the copolymer, of another monomer copolymerizable therewith.

Examples of the alkyl (meth)acrylate include butyl, hexyl, octyl, 2-ethylhexyl, nonyl, decyl, lauryl and stearyl (meth)acrylates. The ester chain of them may be straight-chain or branched.

Examples of the another monomer copolymerizable with the above-exemplified ester include functional monomers, for example, carboxyl group-containing unsaturated monomers such as (meth)acrylic acid, maleic acid, fumaric acid and crotonic acid, hydroxyalkyl (meth)acrylates such as 2-hydroxyethyl (meth)acrylate and 3-hydroxypropyl (meth)acrylate, (meth)acrylamides and derivatives thereof such as (meth)acrylamide, dimethyl (meth)acrylamide and diethyl (meth)acrylamide, N-alkoxyalkyl (meth)acrylamides such as N-butoxymethyl (meth) acrylamide and N-ethoxymethyl (meth)acrylamide, N,N-alkylaminoalkyl (meth)acrylates such as N,N-dimethylaminoethyl (meth)acrylate and acid-amido group containing unsaturated monomers such as N-vinyl pyrrolidone. In addition to these functional monomers, non-functional monomers such as vinyl acetate, styrene or acrylonitrile can also be used for copolymerization.

Examples of the rubber-based pressure-sensitive adhesive include those obtained by incorporating a tackifier resin such as a rosin-based resin, terpene-based resin, coumarone-indene-based resin, terpene-phenol-based resin or petroleum resin in a main polymer such as natural rubber, polyisobutylene, polyisoprene, polybutene, styrene-isoprene block copolymer or styrene-butadiene block copolymer. The rubber-based pressure-sensitive adhesive having the above-described composition can also contain a softener such as liquid polybutene, mineral oil, lanolin, liquid isoprene or fatty acid ester, a filler such as titanium oxide or zinc oxide and/or antioxidant such as butylhydroxytoluene as needed. Such an additive does not cause any harm even if incorporated in the above-described acrylic pressure-sensitive adhesive. When a softener is added to the acrylic pressure-sensitive adhesive, crosslinking treatment with a polyfunctional polyisocyanate, polyfunctional epoxy compound or an aluminum chelate compound as needed is preferred.

Examples of the silicone-based pressure-sensitive adhesive include those composed mainly of dimethyl polysiloxane.

The pressure-sensitive adhesive layer formed of such a pressure-sensitive adhesive preferably has a thickness of 10 to 120 $\mu$m, more preferably 20 to 80 $\mu$m. When the thickness is less than 10 μm, sufficient fixing property is not always available when a medical adhesive tape using it is applied to the skin. Thickness exceeding 120 μm on the other hand presumably causes an irritation upon peeling of the medical adhesive tape from the skin owing to too strong adhesion. In addition, an excessively thick adhesive increases the production cost and is therefore disadvantageous. The above-described pressure-sensitive adhesive is applied to the base film in accordance with the conventionally known method, whereby a pressure-sensitive adhesive layer is formed.

The medical adhesive tape of the present invention thus obtained is rolled and used as a rolled adhesive plaster (surgical tape) or dressing.

Alternatively, it is cut into pieces of a proper size and can be used as a first-aid adhesive tape equipped with a liquid absorbing pad at the central region on the surface of the pressure-sensitive adhesive layer. As the liquid adsorbing pad, conventionally known one, for example, gauze, woven fabric, nonwoven fabric, composite between absorbent cotton and nonwoven fabric and a composite between absorbent cotton and knit net can be employed. Its size differs depending on the size of the target medical adhesive tape, but is preferred to adjust so that 2 to 3 mm of the pressure-sensitive adhesive layer of the medical adhesive tape is exposed around the liquid absorbing pad.

To prevent the surface of the pressure-sensitive adhesive layer of the first-aid adhesive tape of the invention from contamination, it is preferably covered with a separator until use. In this case, a separator using a silicone-based release agent is preferred, because it improves the releasability with the pressure-sensitive adhesive layer containing an organosiloxane-based polymer.

The medical adhesive tape thus obtained has excellent flexibility and stress relaxation and does not bring about a feeling of physical disorder when it is applied to the skin. The skin surface however becomes stuffy when the medical adhesive tape is applied to the skin surface for long hours, resulting in the possibility of causing irritation. In such a case, it is preferred to perforate both the medical adhesive tape base film and pressure-sensitive adhesive layer within an extent not lowering the mechanical strength of the medical adhesive tape. This perforating treatment makes it possible to cut the rolled adhesive plaster of the invention by hands upon use. The perforating treatment can be effected using a perforating roll, or by punching or exposure to laser. The pore size is preferably about 0.2 to 3 mm.

The present invention will hereinafter be described in further detail by Examples, wherein all designations of "parts" or "part" mean "parts by weight" or "part by weight" and those of "%" mean "weight %".

EXAMPLES AND COMPARATIVE EXAMPLES

<Preparation of Resin Pellets>

An amorphous polyolefin resin, an inorganic filler and a thermoplastic elastomer were charged, as resins to be used for the preparation of layer A, at amounts as specified in Table 1 and kneaded in a kneader of 200° C. for 5 to 10 minutes, whereby resin pellets A were prepared. Random polypropylene and a thermoplastic elastomer were charged as resins to be used for the preparation of layer B at amounts as specified in Table 2 and kneaded in a kneader of 200° C. for 5 to 10 minutes, whereby resin pellets B were prepared.

TABLE 1

Composition of Layer A

| | Main component of film | | | | Inorganic filler | | Thermoplastic polymer | |
| --- | --- | --- | --- | --- | --- | --- | --- | --- |
| | Kind | Amount | Kind | Amount | Kind | Amount | Kind | Amount |
| A1 | Random P.P. MFR: 1 | 25 | Propylene.butene-1 copolymer Melt Viscosity (190° C.): 8500 mpa · s | 25 | Talc, particle size: 5 μm | 40 | Hydrogenated styrene.butadiene copolymer MFR: 10 | 10 |
| A2 | Random P.P. MFR: 1 | 25 | Propylene.ethylene copolymer Melt Viscosity (190° C.): 8500 mpa · s | 25 | Talc, particle size: 5 μm | 30 | Hydrogenated styrene.butadiene copolymer MFR: 10 | 10 |
| A3 | Random P.P. MFR: 1 | 20 | Propylene.butene-1 copolymer Melt Viscosity (190° C.): 8500 mpa · s | 30 | Zeolite, particle size: 2.8 μm | 40 | Ethylene.butene-1 copolymer MFR: 3.5 | 15 |
| A4 | Random P.P. MFR: 1 | 25 | Propylene.butene-1 copolymer Melt Viscosity (190° C.): 8500 mpa · s | 25 | Talc, particle size: 5 μm | 40 | Hydrogenated styrene.butadiene copolymer MFR: 10 | 10 |

MFR: Melt flow rate (g/10 min, as measured at 230° C. under load of 21.18N)

<Preparation of Film>

A medical adhesive tape base film of Examples was prepared in accordance with a known T-die method by using a three-layer extruder. Upon preparation, the temperature of the cylinder of the extruder was adjusted to fall within a range of 150 to 240° C. according to the kind of a resin. Medical adhesive tape base films of Examples 1 to 6 were obtained by extruding each of the compositions to have a predetermined thickness ratio and forming films to have a total thickness of 80 μm. Both sides of the resulting medical adhesive tape base films were embossed by bonding an embossing roll thereto under pressure rightly after extrusion but before cooling.

TABLE 2

| | Components of layer B (surface to have a pressure-sensitive adhesive laminated thereover) | | | | Component of layer A | Components of layer B (surface free from laminating thereover a pressure-sensitive adhesive) | | | |
|---|---|---|---|---|---|---|---|---|---|
| | Base | Amount | Thermoplastic polymer | Amount | | Base | Amount | Thermoplastic polymer | Amount |
| Ex. 1 | Random P.P. MFR: 11 | 70 | Ethylene.butene-1 copolymer MFR: 3.5 | 30 | A1 | Random P.P. MFR: 11 | 100 | — | — |
| Ex. 2 | Random P.P. MFR: 11 | 80 | Hydrogenated styrene.butadiene copolymer MFR: 10 | 20 | A2 | Random P.P. MFR: 11 | 100 | — | — |
| Ex. 3 | Random P.P. MFR: 11 | 70 | Styrene.vinyl isprene copolymer MFR: 0.6 | 30 | A3 | Random P.P. MFR: 11 | 100 | — | — |
| Ex. 4 | Random P.P. MFR: 11 | 80 | Ethylene.butene-1 copolymer MFR: 3.5 | 20 | A4 | Random P.P. MFR: 11 | 80 | Ethylene.butene-1 copolymer MFR: 3.5 | 20 |
| Ex. 5 | | | — | | A4 | Random P.P. MFR: 11 | 100 | — | — |
| Ex. 6 | Random P.P. MFR: 11 | 100 | — | — | A4 | | | — | |
| Comp. Ex. 1 | | | — | | A4 | | | — | |
| Comp. Ex. 2 | Monolayer film of a polyethylene and an ethylene.vinyl acetate copolymer mixture | | | | | | | | |
| Comp. Ex. 3 | Monolayer film of an ethylene.methyl methacrylate copolymer | | | | | | | | |
| Comp. Ex. 4 | Monolayer film of polyvinyl chloride | | | | | | | | |

Film Thickness

In Examples 1 to 4: layer B/layer A/layer B=1/10/1=80 (μm) in total.

In Examples 5 and 6: layer A/layer B=10/1=80 (μm) in total.

In Comparative Examples 1 to 4: a single layer having a thickness of 80 μm

<Preparation of a Pressure-sensitive Adhesive>

(Pressure-sensitive Adhesive 1)

In ethyl acetate used as a polymerization solvent, 95 parts of isooctyl acrylate and 5 parts of acrylic acid were copolymerized, whereby a pressure-sensitive adhesive solution having a solid concentration of 35% was obtained.

(Pressure-sensitive Adhesive 2)

To 100 parts of the pressure-sensitive adhesive 1 obtained above, 70 parts of isopropyl myristate as a plasticizer and 0.2 part of a trifunctional polyisocyanate as an external crosslinking agent were added after dilution with ethyl acetate, whereby a solution of a pressure-sensitive adhesive having a solid concentration of 30% was obtained.

<Preparation of a Medical Adhesive Tape>

Over a separator having one side subjected to releasability imparting treatment with a silicone resin, the pressure-sensitive adhesive solution obtained above was applied and then dried to give a dry thickness of about 50 μm, whereby a pressure-sensitive adhesive layer was formed. The resulting pressure-sensitive adhesive layer was then transferred and laminated over the medical adhesive tape base film obtained in each of Examples 1 to 6, whereby a medical adhesive tape was obtained.

<Evaluation Test>

The medical adhesive tape base films and medical adhesive tapes thus prepared were subjected to an evaluation test concerning the items which will be described below. As a test sample, a film cut into a size of 20 mm wide and 40 mm long was employed. Measurement of the below-described items except application test was conducted using a tensile tester under the conditions of a distance between chucks of 20 nm, temperature of 23±2° C. and relative humidity of 65±15%. The monolayer base films of Comparative Examples which were shown in Table 2 were subjected to a similar test.

(Initial Stress)

Each of the base films was stretched at a pulling rate of 300 mm/min to determine a strain-stress curve. From this strain-stress curve, the initial stress (N/20 mm) was found.

(Stress Relaxation Ratio)

A tensile test was conducted in a similar manner to the test of an initial stress. Variations in the value of tensile stress with the passage of time were measured by stretching each of the films until the film showed a 10% elongation and a stress relaxation ratio (%) was determined from the following equation:

Stress relaxation ratio (%)=(Stress after 5 minutes/initial tensile stress)×100 wherein, the initial tensile stress means the maximum tensile stress during the time just after initiation of pulling until 10% elongation.

(Half-stress Period)

A tensile test was conducted in a similar manner to the test of an initial stress and each film was stretched to 10% elongation. Variations in tensile stress with the passage of time were measured to determine a stress relaxation curve. From this curve, a time (second) required to reduce the tensile stress to half of the initial tensile stress was determined. These properties of the base films are shown collectively in Table 3.

(Properties of a Medical Adhesive Tape Upon Application to the Skin)

Each of the medical adhesive tapes produced using base films of Examples 1 to 4 and Comparative Examples 2 to 4 was cut into a piece of 5 cm×5 cm and was applied for 8 hours to the elbow (bending portion) of 10 normal volunteers. Feeling upon application and adhesion to the skin were evaluated in accordance with the 5-stage system. The results are shown in Table 4. In Table 4, the average point of 10 volunteers is shown.

(Fixation of Tube)

Each of surgical tapes produced using the medical adhesive tape base films of Examples 1, 4, 5 and 6 and Comparative Example 1 was cut into a size of 12 mm×60 mm. A silicone tube having an outer diameter of 5 mm was bent into a U-shape and fixed to the inside of the antebrachium of 10 normal volunteers with the resulting surgical tape. The fixing property of the tape was evaluated by the time (minute) until the tape release occurred by the restoring power of the tube. The results are shown in Table 5.

(Properties of a First-aid Adhesive Tape Upon Application to the Skin)

A medical adhesive tape prepared using each of the medical adhesive tape base films of Examples 1, 2 and 4 and Comparative Examples 2 to 4 was cut into a size of 19 mm×72 mm. A gauze pad of 12 mm×20 mm was disposed in a central region on the surface of the pressure-sensitive adhesive of the medical adhesive tape, whereby a first-aid adhesive tape was prepared. Ten normal volunteers were asked to wrap the first-aid adhesive tape thus obtained around their second joint of a finger for 6 hours and also to apply it to their antebrachium for 8 hours. The feeling upon application, skin adhesion and skin stimulation were evaluated by the 5-stage system. The results are shown in Table 6. The numeral shown in Table 6 is an average point of 10 volunteers.

<Evaluation Results>

From Table 3, it has been found that each of the medical adhesive tape base films according to the invention had an initial stress almost equal to or higher than the conventional polyethylene film, but not so high as to cause a problem upon practical use; the stress relaxation ratio was lower than that of the conventional polyethylene film and almost equal to that of a polyvinyl chloride film; and the stress-half time was not shorter than that of a polyvinyl chloride film, but by far shorter than that of the conventional polyethylene film.

From Tables 4 and 6, it has been understood that each of the medical adhesive tapes obtained using the base films of the invention was superior to that produced using the conventional polyethylene film in feeling upon application, skin adhesion and skin stimulation, and their performance was almost similar to that produced using a polyvinyl chloride film.

From Table 5, it has been found that in the case where a pressure-sensitive adhesive layer was directly laminated over layer A composed of amorphous polyolefin, breakage of anchorage were observed from some pressure-sensitive adhesives, suggesting that a medical adhesive tape suited for fixing a tube having a high restoring power was not formed (Example 5 and Comparative Example 1).

From Table 5, on the other hand, it has been found that when a pressure-sensitive adhesive layer was laminated over layer B, no breakage of anchorage was observed and a tube having a restoring power could be fixed sufficiently.

TABLE 3

Test results of the properties of base films

| Base film | Initial stress (N/20 mm) | Stress relaxation ratio (%) | Stress-half time (s) |
|---|---|---|---|
| Example 1 | 13.8 | 36 | 16 |
| Example 2 | 13.6 | 39 | 29 |
| Example 3 | 11.7 | 35 | 14 |
| Example 4 | 13.0 | 36 | 16 |
| Comp. Ex. 2 | 11.9 | 67 | at least 500 |
| Comp. Ex. 3 | 7.5 | 65 | at least 500 |
| Comp. Ex. 4 | 8.5 | 17 | 2 |

TABLE 4

Test results of medical adhesive tape upon application

| Base film | Pressure-sensitive adhesive | Feeling upon application | Skin adhesion |
|---|---|---|---|
| Example 1 | 1 | 4.5 | 4.2 |
| Example 2 | 1 | 4.4 | 4.6 |
| Example 3 | 1 | 4.8 | 4.7 |
| Example 4 | 1 | 4.6 | 4.5 |
| Comp. Ex. 2 | 1 | 3.7 | 4.1 |
| Comp. Ex. 3 | 1 | 3.5 | 4.3 |
| Comp. Ex. 4 | 1 | 4.7 | 3.5 |

Evaluation:
5 (Excellent) - 4 - 3 (fair) - 2 - 1 (poor)

TABLE 5

Test results of tube fixation

| Base film | Pressure-sensitive adhesive | Fixation |
|---|---|---|
| Example 1 | 2 | ≧180 minutes |
| Example 4 | 2 | ≧180 minutes |
| Example 5 | 2 | * |
| Example 6 | 2 | ≧180 minutes |
| Comparative Example 1 | 2 | * |

*: Anchorage of the pressure-sensitive adhesive was broken during the test.

TABLE 6

Test results of first-aid adhesive tape upon application

| Base film | Pressure-sensitive adhesive | Feeling upon application | | Skin adhesion | | Skin stimulation |
|---|---|---|---|---|---|---|
| | | Finger | Antebrachium | Finger | Antebrachium | Antebrachium |
| Ex. 1 | 1 | 4.2 | 4.3 | 4.5 | 4.7 | 4.3 |
| Ex. 2 | 1 | 4.5 | 4.7 | 4.3 | 4.3 | 4.0 |
| Ex. 4 | 1 | 4.7 | 4.8 | 4.2 | 4.6 | 4.3 |
| Comp. Ex. 2 | 1 | 3.8 | 4.1 | 3.8 | 4.5 | 3.9 |
| Comp. Ex. 3 | 1 | 3.7 | 4.3 | 4.1 | 4.2 | 3.5 |

TABLE 6-continued

Test results of first-aid adhesive tape upon application

| Base film | Pressure-sensitive adhesive | Feeling upon application | | Skin adhesion | | Skin stimulation |
|---|---|---|---|---|---|---|
| | | Finger | Antebrachium | Finger | Antebrachium | Antebrachium |
| Comp. Ex. 4 | 1 | 4.5 | 4.8 | 4.5 | 4.7 | 4.1 |

Evaluation:
5 (excellent) - 4 - 3 (fair) - 2 - 1 (poor)

The medical adhesive tape base film according to the present invention is obtained by laminating, over at least one side of layer A made of amorphous polyolefin, layer B made of a polypropylene-based resin so that it is well balanced in tensile strength, flexibility and stress relaxation compared with the conventional polyolefin film and its properties are rather close to those of a polyvinyl chloride film.

By incorporating a thermoplastic elastomer in layer B to be laminated over layer A, properties of the medical adhesive tape base film such as tensile strength, flexibility and stress relaxation can be made closer to those of a polyvinyl chloride film.

It is preferred to laminate layer B over both sides of layer A, but a medical adhesive tape exhibiting a further improved performance upon application is available by incorporating the thermoplastic elastomer in either one of two layers B. It is needless to say that formation of a pressure-sensitive adhesive layer on the thermoplastic-elastomer-containing layer B makes it possible to reduce the occurring frequency of breakage of anchorage and to prevent bleed-through of the low-molecular-weight substance due to its transfer from layer A to the pressure-sensitive adhesive layer.

As described above, a medical adhesive tape base film substitutable for a conventional polyvinyl chloride film can be provided according to the present invention. Medical adhesive tapes suited for medical use such as adhesive plaster and first-aid adhesive tape which have excellent tensile strength, flexibility and stress relaxation and are not inferior to those made of a polyvinyl chloride film can be provided using this base film for a medical adhesive tape.

While the invention has been described in detail and with reference to specific embodiments thereof, it will be apparent to one skilled in the art that various changes and modifications can be made therein without departing from the spirit and scope thereof.

What is claimed is:

1. A medical adhesive tape useful for forming an adhesive plaster, said tape comprising a base film and a pressure-sensitive adhesive layer, wherein
   said base film is obtained by laminating on each side of a layer A, a layer B,
   said layer A comprising an amorphous polyolefin, a thermoplastic elastomer and an inorganic filler selected from the group consisting of talc and zeolite,
   each of said layers B comprising a polypropylene-based resin, wherein one of said layers B contains a thermoplastic elastomer and the other one of said layers B does not contain a thermoplastic elastomer, and
   at least one of said layer A and said layer B comprising, as said thermoplastic elastomer, a polyolefin thermoplastic elastomer, and
   said pressure-sensitive adhesive layer is laminated directly on said layer B containing the thermoplastic elastomer, or on an embossed or corona-discharge treated or primer pre-treated surface of layer B containing the thermoplastic elastomer.

2. The medical adhesive tape according to claim 1, wherein said amorphous polyolefin is at least one selected from the group consisting of amorphous polypropylene and random copolymers of ethylene and/or butene-1 and propylene.

3. The medical adhesive tape according to claim 1, wherein said layer A further comprises crystalline polyolefin.

4. The medical adhesive tape according to claim 1, wherein said thermoplastic elastomer is an ethylene-butene copolymer and/or a styrene-butadiene copolymer.

5. The medical adhesive tape according to claim 1, wherein the polypropylene-based resin of each of said layers B is ethylene-containing random polypropylene.

6. The medical adhesive tape according to claim 1, wherein said layer A has a thickness of 10 to 100 µm.

7. The medical adhesive tape according to claim 1, wherein each of said layers B has a thickness of 2 to 20 µm.

8. The medical adhesive tape according to claim 1, wherein the surface of said base film is embossed, subjected to corona discharge treatment or treated with a primer.

9. The medical adhesive tape according to claim 1, wherein said pressure-sensitive adhesive layer is formed on an embossed or corona-discharge treated or primer pre-treated surface.

10. The medical adhesive tape according to claim 1, wherein said polyolefin thermoplastic elastonier is an ethylene-butene copolymer.

* * * * *